United States Patent [19]

Wright, Jr. et al.

[11] Patent Number: 4,782,064

[45] Date of Patent: Nov. 1, 1988

[54] 2-HETEROARYL-ALKYL-1H-BENZ[DE]-ISOQUINOLINE-1,3(2H)-DIONES

[75] Inventors: William B. Wright, Jr., Woodcliff Lake; Andrew S. Tomcufcik, Old Tappan, both of N.J.; Nancy H. Eudy, Cornwall-On-Hudson, N.Y.

[73] Assignee: American Cyanamid Co., Stamford, Conn.

[21] Appl. No.: 887,688

[22] Filed: Jul. 21, 1986

[51] Int. Cl.$^4$ ............... A61K 31/47; C07D 401/06; C07D 249/08; C07D 233/61
[52] U.S. Cl. ................... 514/296; 548/262; 548/341; 546/99; 546/100
[58] Field of Search ............ 546/99, 100; 514/296

[56] References Cited

U.S. PATENT DOCUMENTS

| | | | |
|---|---|---|---|
| 3,625,947 | 1/1968 | Noguchi | 546/99 |
| 3,840,838 | 4/1974 | Mingasson | 546/99 |
| 3,935,227 | 1/1976 | Wade | 546/99 |

FOREIGN PATENT DOCUMENTS

| | | | |
|---|---|---|---|
| 2331307 | 1/1975 | Fed. Rep. of Germany | 546/99 |
| 1344883 | 10/1963 | France | 546/99 |
| 45-2668 | 1/1970 | Japan | 546/99 |

*Primary Examiner*—Mark L. Berch
*Attorney, Agent, or Firm*—H. G. Jackson

[57] ABSTRACT

This invention concerns novel 2-heteroarylalkyl-1H-benz[de]isoquinoline-1,3(2H)-diones which are useful as inhibitors of thromboxane synthetase and/or as hypotensive agents in the treatment of hypertension and myocardial ischemia.

17 Claims, No Drawings

2-HETEROARYL-ALKYL-1H-BENZ[DE]-ISOQUINOLINE-1,3(2H)-DIONES

BRIEF SUMMARY OF THE INVENTION

The present invention relates to new organic compounds and, more particularly, is concerned with novel 2-heteroaryl-alkyl-1H-benz[de]isoquinoline-1,3(2H)-diones which may be represented by the following structural formula:

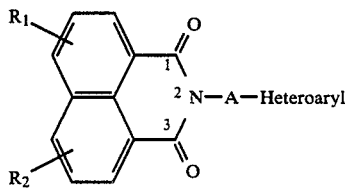

wherein A is a divalent moiety of the formula: —$C_nH_{2n}$— or —$CH_2CH=CHCH_2$— where n is an integer from 3 to 8, inclusive; $R_1$ and $R_2$ may be the same or different and may be selected from the group consisting of hydrogen, halogen, alkoxy having from one to four carbon atoms, alkyl having from one to four carbon atoms, nitro and amino; and where Heteroaryl is

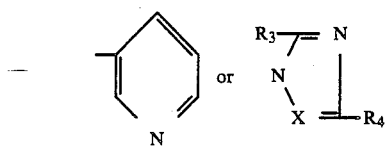

wherein $R_3$ and $R_4$ may be hydrogen, alkyl having from one to four carbon atoms or phenyl; and X is CH or N.

A preferred embodiment of the present invention may be represented by the following structural formula:

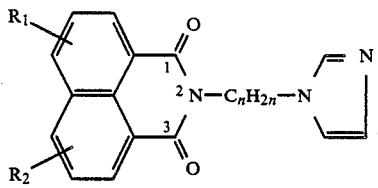

wherein $R_1$ and n are as hereinbefore defined. Most preferably $R_1$ is hydrogen or chlorine and n is 3-5.

The organic bases of this invention form non-toxic acid-addition salts with a variety of pharmacologically acceptable organic and inorganic salt-forming reagents. Thus, acid-addition saits, formed by admixture of the organic free base with one or more equivalents of an acid, suitably in a neutral solvent, are formed with such acids as sulfuric, phosphoric, hydrochloric, hydrobromic, maleic, sulfamic, citric, lactic, malic, succinic, tartaric, acetic, benzoic, fumaric, gluconic, ascorbic, and the For purposes of this invention the free bases are equivalent to their non-toxic acid-addition salts. The acid-addition salts of the organic bases of the present invention are, in general, relatively soluble in water, methanol and ethanol but relatively insoluble in non-polar organic solvents such as diethyl ether, benzene toluene and the like.

DETAILED DESCRIPTION OF THE INVENTION

The novel compounds of the present invention may be readily prepared as set forth in the following reaction scheme wherein $R_1$, $R_2$, n, A and Heteroaryl are as hereinabove defined:

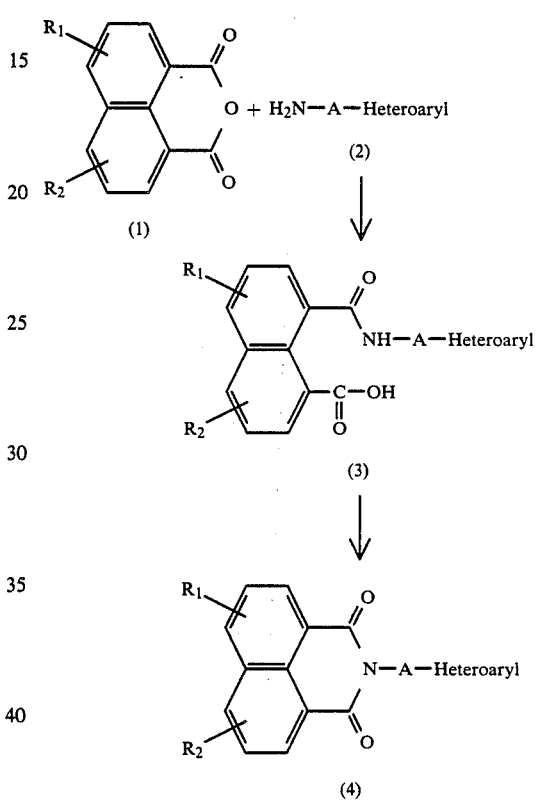

In accordance with this method; an appropriately substituted 1,8-naphthalic anhydride (1) is treated with a heterocyclic alkylamine (2) in an inert solvent such as methylene chloride or ethanol at ambient temperature to form the intermediate amide (3). Heating of (3) above its melting point at a preferred temperature of 130°-180° C. for 30-60 minutes results in the desired amide (4). Alternatively (3) may be heated with a dehydrating mixture such as acetic anhydride and acetic acid to obtain the same compounds (4).

In still another procedure the amide (4) is prepared in one step without isolation of the intermediate (3). In this procedure (1) and (2) are heated at reflux temperature in toluene for 2-5 hours using a dehydrating agent such as a Dean-Stark apparatus and the product (4) is obtained by cooling or concentrating the reaction mixture and washing the product onto a filter with a suitable solvent.

The compounds of this invention may also be prepared by the following procedure:

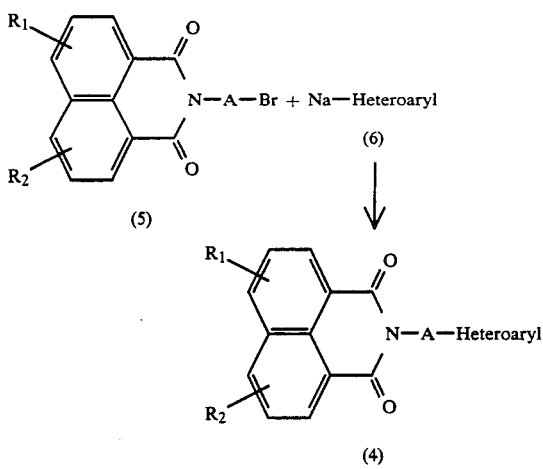

where A and Heteroaryl are as hereinbefore defined. In this procedure (5) is heated at about 100° C. for 4-8 hours in N,N-dimethylformamide with the sodium salt of a heteroaryl compound (6) until reaction has occurred. The reaction mixture is then concentrated and the product (4) is isolated by conventional means.

The compounds of this invention inhibit thromboxane synthetase enzyme without interfering with other enzymes in the arachadonic acid cascade Thus, these compounds are useful in the treatment of diseases characterized by an imbalance of thromboxane $A_2$/prostacyclin, such as ischemic heart disease, transient ischemic attack, thrombosis and migraine. Recent reviews have established the role of the thromboxane/prostacyclin balance in the vascular system [*Cardiovascular diseases: New Trends in Surgical and Medical Aspects*, H. Barnett, P. Paoletti, E. Flamm and G. Brambilla, eds., Elsevier/North-Holland Biomedical Press, pp 137-150 (1981)]. Prostacyclin ($PGI_2$) is a potent vasodilator and platelet aggregation inhibitor, whereas thromboxane ($TXA_2$) is a powerful vasoconstrictor and inducer of platelet aggregation. $TXA_2$ synthesis is catalyzed by thromboxane synthetase enzyme located in, for example, blood platelets. When $TXA_2$ production is increased relative to $PGI_2$, platelet aggregation, thrombosis and vasospasm may occur [*Lancet* (i), 1216 (1977); *Lancet*, 479 (1977); *Science*, 1135 (1976); *Amer. J. Cardiology*, 41, 787 (1978)]. $TXA_2$ synthetase inhibitors have been shown to have anti-thrombotic action superior to that of aspirin [*J. Clin. Invest.*, 65, 400 (1980); *Br. J. Pharmac.*, 76, 3 (1982)].

The role of prostaglandins, including TXA2 and $PGI_2$, in ischemic heart patients has been reviewed [(*Cardiovascular PharmacologY of the Prostaglandins*, A. G. Herman, P. M. Vanhoute, H. Denolin and A. Goosens, eds., Raven Press, New York, pp 361-374 (1982)]. Injection of $TXA_2$ into coronary arteries of guinea pigs and rabbits causes myocardial ischemia and subendocardial necrosis [*Drugs of the Future*, 7, 331 (1982); *Proc. Jap. Acad.*, 53(B), 38 (1977); *Eur. J. Pharmacol.*, 53, 49 (1978). Recent research has demonstrated the beneficial effects of $PGI_2$ and selective inhibition of thromboxane synthetase on ischemic myocardium in canines [*J. Cardiovascular Pharmacoloqy*, 4, 129 (1982)]. Thus compounds which selectively inhibit thromboxane synthetase (and hence $TXA_2$) without adversely affecting $PGI_2$ are useful in the treatment of vascular diseases such as ischemia and migraine. In addition, inhibition of $TXA_2$ formation may effectively treat platelet aggregation and prevent thrombosis.

From Okamoto-Aoki spontaneously hypertensive rats (SHR) (Taconic Farms, Germantown, N.Y.) between 19 and 24 weeks in age, under urethan anesthesia, 10 μl of arterial blood was collected in one ml of 3.2% sodium citrate a polystyrene tube. The blood was diluted with 3 ml cold saline and centrifuged at room temperature for 15 minutes at 460×g. The platelet rich plasma (PRP) was separated. The platelets were isolated by centrifuging the PRP for 10 minutes at 1060×g nd were washed in 4 ml cold oxygenated Krebs phosphate buffer, pH 7.4. The chilled platelets recovered from centrifuging at 800×g for 10 minutes were resuspended in oxygenated Krebs phosphate buffer and diluted to contain $4.5-6.0\times10^4$ platelets/μl.

The inhibition of thromboxane (TX) formation was studied by determining the concentration of thromboxane $B_2$ ($TXB_2$), the stable hydrolysis product of $TXA_2$. Assay samples, prepared on ice, contained 200 μl platelet suspension, 50 μl saline, and 50 μl vehicle or drug under study at a concentration of $10^{-4}M$ (with OKY-1581, UK-3724801, 1-benzylimidazole, and/or indometha standards). The samples were incubated for 10 minutes at 37° C. in a metabolic shaker. The reaction was terminated by immersing the tubes in an ice bath and adding 50 μl of 0.5M citric acid. The samples were centrifuged for 10 minutes in a refrigerated centrifuge and the supernatants thus obtained were decanted and stored at −20° C. The $TXB_2$ content for each sample was determined by a direct radioimmunoassay (RIA) utilizing a $TXB_2$ specific RIA kit purchased from New England Nuclear, Boston, Mass. and results expressed as pg $TXB_2$ formed minute$^{-1}$ sample$^{-1}$, from which the percent inhibition of $TXB_2$ formation was calculated. The results of this test on representative compounds of this invention appear in Table I below.

TABLE I

| Compound | % Inhibition |
|---|---|
| 2-[3-(1H—Imidazol-1-yl)propyl]-1H—benz[de]-isoquinoline-1,3(2H)—dione | 89 |
| 2-[4-(1H—Imidazol-1-yl)butyl]-1H—benz[de]-isoquinoline-1,3(2H)—dione | 96 |
| 2-[5-(1H—Imidazol-1-yl)pentyl]-1H—benz[de]-isoquinoline-1,3(2H)—dione | 100 |
| 2-[8-(1H—Imidazol-1-yl)octyl]-1H—benz[de]-isoquinoline-1,3-(2H)—dione | 98 |
| 2-[3-(1H—Imidazol-1-yl)butyl]-1H—benz[de]-isoquinoline-1,3(2H)—dione | 97 |
| 2-[3-(1H—Imidazol-1-yl)-2-methylpropyl]-1H—benz[de]-isoquinoline-1,3(2H)—dione | 99 |
| 2-[3-(1H—Imidazol-1-yl)-1-phenylpropyl]-1H—benz[de]isoquinoline-1,3(2H)—dione | 97 |
| 2-[3-(4-Methyl-1H—imidazol-1-yl)propyl]-1H—benz[de]isoquinoline-1,3-(2H)—dione | 98 |
| 2-[3-(1H—1,2,4-Triazol-1-yl)propyl]-1H—benz[de]isoquinoline-1,3-(2H)—dione | 96 |
| 2-[4-(3-Pyridinyl)butyl]-1H—benz[de]-isoquinoline-1,3-(2H)—dione | 98 |
| 6-Chloro-2-[3-(1H—imidazol-1-yl)propyl]-1H—benz[de]isoquinoline-1,3-(2H)—dione monohydrochloride | 95 |
| 6-Chloro-2-[4-(1H—imidazol-1-yl)butyl]-1H—benz[de]isoquinoline-1,3-(2H)—dione monohydrochloride | 96 |
| 6-Chloro-2-[5-(1H—imidazol-1-yl)pentyl]-1H—benz[de]isoquinoline-1,3-(2H)—dione | 94 |
| 6-Amino-2-[4-(1H—imidazol-1-yl)butyl]-1H—benz[de]isoquinoline-1,3-(2H)—dione dihydrochloride | 96 |
| 2-[3-(1H—Imidazol-1-yl)propyl]-5-nitro-1H—benz[de]isoquinoline-1,3-(2H)—dione | 100 |
| 2-[4-(1H—Imidazol-1-yl)butyl]-5-nitro-1H— | 97 |

TABLE I-continued

| Compound | % Inhibition |
|---|---|
| benz[de]isoquinoline-1,3-(2H)—dione | |
| 2-[5-(1H—Imidazol-1-yl)pentyl]-5-nitro-1H—benz[de]isoquinoline-1,3-(2H)—dione | 98 |
| 2-[3-(1H—imidazol-1-yl)butyl]-5-nitro-1H—benz[de]isoquinoline-1,3-(2H)—dione | 100 |
| 5-Nitro-2-[3-(2-phenyl-1H—imidazol-1-yl)-propyl]-1H—benz[de]isoquinoline-1,3-(2H)—dione | 89 |
| 5-Nitro-2-[3-(1H—1,2,4-triazol-1-yl)-propyl]-1H—benz[de]isoquinoline-1,3-(2H)—dione | 94 |
| 5-Nitro-2-[2-(3-pyridinyl)ethyl]-1H—benz[de]isoquinoline-1,3-(2H)—dione | 94 |
| 5-Nitro-2-[4-(3-pyridinyl)butyl]-1H—benz[de]isoquinoline-1,3-(2H)—dione | 94 |
| 2-[3-(1H—Imidazol-1-yl)-2-methylpropyl]-5-nitro-1H—benz[de]isoquinoline-1,3-(2H)—dione | 100 |

The novel compounds of the present invention are also active hypotensive agents and were tested for hypotensive activity by the method of P. S. Chan and D. Poorvin, Clinical and Experimental Hypertension, 1 (6), 817–830 (1979). Male, 16 week old, spontaneously hypertensive rats of the Okamoto strain, from Taconic Farms, Germantown, N.Y. having an average mean arterial blood pressure of 160±1.5 mm of mercury were used in the test. One to 3 rats were used per test compound. The rats were dosed by gavage with a test compound, suspended in 2% pre-boiled starch at a concentration of 50 mg/ml, at a dose of 100 mg/kg of body weight or less, with 0.9% sodium chloride loading at a dose of 25 ml/kg of body weight. A second identical dose of the test compound, without sodium chloride loading was given 24 hours later. At 28 hours after the initial dose, the mean arterial blood pressure (MABP) was measured by the method of Chan and Poorvir vide supra. The procedure was repeated in a second and third rat when necessary as specified in the referenced method.

The results of this test on representative compounds of the present invention appear in Table II below.

TABLE II

| Product | MABP/mm Hg (no. of rats) |
|---|---|
| 2-[3-(1H—Imidazol-1-yl)propyl]-1H—benz[de]-isoquinoline-1,3(2H)—dione | 103(2) |
| 2-[4-(1H—Imidazol-1-yl)butyl]-1H—benz[de]-isoquinoline-1,3(2H)—dione | 106(2) |
| 2-[3-(1H—Imidazol-1-yl)butyl]-1H—benz[de]-isoquinoline-1,3(2H)—dione | 120(2) |
| 6-Amino-2-[4-(1H—imidazol-1-yl)butyl]-1H—benz[de]isoquinoline-1,3(2H)—dione dihydrochloride | 115(2) |
| 2-[3-(1H—Imidazol-1-yl)propyl]-5-nitro-1H—benz[de]isoquinoline-1,3(2H)—dione | 97(2) |
| 2-[4-(1H—Imidazol-1-yl)butyl]-5-nitro-1H—benz[de]isoquinoline-1,3-(2H)—dione | 123(1) |
| 5-Nitro-2-[3-(1H—1,2,4-triazol-1-yl)-propyl]-1H—benz[de]isoquinoline-1,3-(2H)—dione | 127(1) |
| 2-[3-(1H—Imidazol-1-yl)-2-methylpropyl]-1H—benz[de]isoquinoline-1,3-(2H)—dione | 134(4) |
| 2-[4-(3-Pyridinyl)butyl]-1H—benz[de]iso-quinoline-1,3(2H)—dione | 137(2) |

The novel compounds of the present invention have been found to be highly useful for inhibiting thromboxane synthetase and also for lowering elevated blood pressure in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units are employed that a total of from about 35 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-alpha-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen or cherry flavoring may be added. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor or the equivalents thereof. Of course, any material used in preparing any dosage unit form should be pharmaceutically pure and substantially nontoxic in the amounts employed.

The following specific examples illustrate the preparation of the compounds of the present invention.

EXAMPLE 1

2-[4-(1H-Imidazol-1-yl)butyl]-1H-benz-[de]isoquinoline-1,3(2H)-dione

A mixture of 3.0 g of 1,8-naphthalic anhydride, 50 ml of methyline chloride and 2.1 g of 1H-imidazole-1-butanamine was stirred at room temperature for 20 hours. The insoluble product was isolated by filtration, washed with methlene chloride and then ether and dried in vacuo. The solid was placed in a round-bottom flask and immersed in an oil bath at 150° C., and the temperature was increased over a 45 minute period to 165° C. The reaction mixture was allowed to cool and the residue was triturated with ethyl acetate and recovered by filtration. After recrystallization from ethanol, the desired product melted at 153°–155° C.

Following the procedure of this example and using the appropriate diamine, the products of Examples 2–9 were obtained as set forth in Table III.

EXAMPLE 10

6-Ethyl-2-[4-(1H-imidazol-1-yl)-butyl]-1H-benz-[de]isoquinoline-1,3(2H)-dione

The above compound is obtained when 4-ethyl-1,8-naphthalic anhydride is substituted for 1,8-naphtalic anhydride in the procedure of Example 1.

EXAMPLE 11

2-[4-(1H-imidazol-1-yl)butyl]-5-methyl-1H-benz-[de]isoquinoline-1,3(2H)-dione

When 3-methyl-1,8-naphtalic anhydride is reacted with 1H-imidazole-1-butanamine by the procedure of Example 1, the above compound is obtained.

EXAMPLE 12

2-[4-(1H-imidazol-1-yl)butyl]6-methoxy-1H-benz-[de]isoquinoline-1,3(2H)-dione

This compound is obtained when 4-methoxy-1,8-naphthalic anhydride and 1H-imidazole-1-butanamine are allowed to react by the procedure of Example 1.

EXAMPLE 13

6-Chloro-2-[4-(1H-imidazol-1-yl)butyl]-1H-benz-[de]isoquinoline-1,3(2H)-dione monohydrochloride A mixture of 3.49 g of 4-chloro-1,8-naphthalic anhydride, 50 ml of ethanol and 2.1 g of 1H-imidazol-1butanamine as stirred at room temperature for 5 hours and concentrated. The residue was washed on to a funnel with a little ethanol, washed with ether and dried in vacuo. The solid material, 3.72 g, was mixed with 15 ml of acetic anhydride and 5 ml of acetic acid and heated at 110°–120° C. in an oil bath for 6 hours. The reaction mixture was concentrated and shaken with 20 ml of 1N sodium hydroxide and 150 ml of methylene chloride and the layers were separated. The organic layer was washed with water, dried over magnesium sulfate and concentrated. The residue was recrystallized from ethyl acetate to obtain the desired product, mp 138°–140° C.

When this material was treated with ethanolic hydrogen chloride, the hydrochloride salt, mp 228°–230° C., was obtained.

Following the procedure of Example 13 and using the appropriate diamine, the products of Examples 14–15 were obtained as set forth in Table IV.

TABLE III

| Example | Diamine | Product | MP °C. |
|---|---|---|---|
| 2 | 1H—imidazole-1-propanamine | 2-[3(1H—imidazol-1-yl)propyl]-1H—benz[de]isoquinoline-1,3(2H)—dione | 165–167 |
| 3 | 1H—imidazole-1-pentanamine | 2-[5-(1H—imidazol-1-yl)pentyl)-1H—benz[de]isoquinoline-1,3(2H)—dione | 117–119 |
| 4 | 3-(1H—imidazol-1-yl)-butanamine | 2-[3-(1H—imidazol-1-yl)butyl]-1H—benz[de]isoquinoline-1,3(2H)—dione | 175–177 |
| 5 | 3-(1H—imidazol-1-yl)-2-methyl-propanamine | 2-[3-(1H—imidazol-1-yl)-2-methyl-propyl]-1H—benz[de]isoquinoline-1,3(2H)—dione | 145–147 |
| 6 | 3-(1H—imidazol-1-yl)-1-phenyl-propanamine | 2-[3-(1H—imidazol-1-yl)-1-phenyl-propyl]-1H—benz[de]isoquinoline-1,3(2H)—dione | 191–193 |
| 7 | 3-(4-methyl-1H—imidazol-1-yl)-propanamine | 2-[3-(4-methyl-1H—imidazol-1-yl)-propyl]-1H—benz[de]isoquinoline-1,3(2H)—dione | 133–136 |
| 8 | 3-(1H—1,2,4-triazol-1-yl)-propanamine | 2-[3-(1H—1,2,4-triazol-1-yl)-propyl]-1H—benz[de]isoquinoline-1,3(2H)—dione | 161–163 |
| 9 | 4-(3-pyridinyl)butanamine | 2-[4-(3-pyridinyl)butyl]-1H—benz[de]isoquinoline-1,3(2H)—dione | 111–113 |

TABLE IV

| Example | Diamine | Product | MP °C. |
|---|---|---|---|
| 14 | 1H—imidazole-1-propanamine | 6-Chloro-2-[3(1H—imidazol-1-yl)-propyl]-1H—benz[de]isoquinoline-1,3(2H)—dione monohydrochloride | 271–273 |
| 15 | 1H—imidazole-1-pentanamine | 6-Chloro-2-[5-(1H—imidazol-1-yl)-pentyl]-1H—benz[de]isoquinoline-1,3(2H)dione monohydrochloride | 226–228 |

Following the procedure of Example 13 and reacting the appropriate 1,8-naphthalic anhydride with 1H-imidazole-1-butanamine the products of Examples 16–18 are obtained as set forth in Table V.

TABLE V

| Ex. | 1,8-naphthalic anhydride | Product |
|---|---|---|
| 16 | 3,5-dichloro | 5,7-dichloro-2-[4-(1H—imidazol-1-yl)-butyl]-1H—benz[de]isoquinoline-1,3-(2H)—dione |
| 17 | 4,5-dibromo | 6,7-dibromo-2-[4-(1H—imidazol-1-yl)-butyl]-1H—benz[de]isoquinoline-1,3(2H)—dione |
| 18 | 4-fluoro | 6-Fluoro-2-[4-(1H—imidazol-1-yl)-butyl]-1H—benz[de]isoquinoline-1,3(2H)—dione |

EXAMPLE 19

2-[8-(1H-Imidazol-1-yl)octyl]-1H-benz[de]isoquinoline-1,3(2H)-dione

This compound, mp 120°–122° C., was obtained when 1,8-naphthalic anhydride was reacted with 1H-imidazole-octanamine by the procedure of Example 13.

EXAMPLE 20

6-Amino-2-(4-bromobutyl)-1H-benz[de]isoquinoline-1,3(2H)-dione

A suspension of 10.6 g of 6-amino-1H-benz[de]-isoquinoline-1,3(2H)-dione in 250 ml of dimetnylformamide was stirred as 2.6 g of 50% sodium hydride in mineral oil was added. The initial orange suspension turned deep red in color. After ten minutes, a solution of 27 g of 1,4-dibromobutane in 50 ml of dimethylformamide was added. A slightly exothermic reaction was noted, and a deep red solution resulted. The mixture was then stirred at room temperature for sixteen hours, and drowned into 600 ml of cold water. A tarry brown precipitate was obtained, and on standing, bright yellow crystals developed in the supernatant. These were collected and recrystallized from aqueous alcohol to yield the pure title compound mp 175°–176° C. The brown precipitate required several recrystallizations from aqueous alcohol to afford more of the pure title compound.

EXAMPLE 21

6-Amino-2-[4-(1H-imidazol-1-yl)-]-1H-benz[de]isoquinoline-1,3(2H)-dione, dihydrochloride A mixture of 1.0 g of imidazole, 100 ml of N,N-dimethylformamide and 0.6 g of 50% sodium hydride was stirred for 30 minutes and 3.5 g of 6-amino-2-(4-bromobutyl)-1H-benz[de]isoquinoline-1,3(2H)-dione was added. The reaction mixture was heated on the steam bath for 8 hours, concentrated, and treated with 150 ml of water and 250 ml of methylene chloride. The solvents were decanted and the residue was stirred for 18 hours with 250 ml of ethanol. The mixture heated to boiling, clarified, treated with 15 ml of 2N ethanolic hydrogen chloride and cooled. A small amount of solid material was filtered off. Acetone was added and the precipitated dihydrochloride salt was removed by filtration and dried in vacuo. The desired material melted at 255°–258° C.

EXAMPLE 22

2-[4-(1H-Imidazol-1-yl)butyl]-5-nitro-1H-benz[de]isoquinoline-1,3(2H)-dione

A suspension of 4.86 g of 3-nitro-1,8-naphthalic anhydride in 200 ml of toluene was heated and then allowed to cool to room temperature. A solution of 3.0 g of 1H-midazole-1-butanamine in 20 ml of toluene was added dropwise over about 5 minutes and the mixture was heated at reflux temperature for 165 minutes, using a Dean-Stark trap to remove water. After cooling overnight, the product was removed by filtration, washed with 5% sodium bicarbonate solution, dried and recrystallized from methylene chloride/hexane. The melting point was 193°–195° C. 5 Following the procedure of Example 22 and using the appropriate diamine, the products of Examples 23–30 were obtained as set forth in Table VI.

TABLE VI

| Example | Diamine | Product | MP °C. |
|---|---|---|---|
| 23 | 1H—imidazole-1-propanamine | 2-[3-(1H—imidazol-1-yl)propyl]-5-nitro-1H—benz[de]isoquinoline-1,3(2H)—dione | 208–210 |
| 24 | 1H—imidazole-1-pentanamine | 2-[5-(1H—imidazol-1-yl)pentyl)-5-nitro-1H—benz[de]isoquinoline-1,3(2H)—dione | 160–162 |
| 25 | 3-(1H—imidazol-1-yl)-butanamine | 2-[3-(1H—imidazol-1-yl)butyl]-5-nitro-1H—benz[de]isoquinoline-1,3(2H)—dione | 204–206 |
| 26 | 3-(1H—imidazol-1-yl)-2-methyl-propanamine | 2-[3-(1H—imidazol-1-yl)-2-methyl-propyl]-5-nitro-1H—benz[de]-isoquinoline-1,3(2H)—dione | 254–256 |
| 27 | 3-(2-phenyl-1H—imidazol-1-yl)-propanamine | 5-Nitro-2-[3-(2-phenyl-1H—imidazol-1-yl)propyl]-1H—benz[de]-isoquinoline-1,3(2H)—dione | 184–186 |
| 28 | 3-(1H—1,2,4-triazol-1-yl)-propanamine | 5-Nitro-2-[3-(1H—1,2,4-triazol-1-yl)propyl]-1H—benz[de]isoquino- | 176–178 |

TABLE VI-continued

| Example | Diamine | Product | MP °C. |
|---|---|---|---|
| | | line-1,3(2H)—dione | |
| 29 | 2-(3-pyridinyl)-ethanamine | 5-Nitro-2-[2-(3-pyridinyl)ethyl]-1H—benz[de]isoquinoline-1,3(2H)—dione | 216–217 |
| 30 | 4-(3-pyridinyl)-butanamine | 5-nitro-2-[4-(3-pyridinyl)butyl]-1H—benz[de]isoquinoline-1,3(2H)—dione | 165–167 |

EXAMPLE 31

2-[4-(1H-Imidazol-1-yl)-2-butenyl]1H-benz-[de]isoquinoline-1,3(2H)-dione

The above compound is obtained when 1,8-napthalic anhydride is reacted with 4-(1H-imidazol-1-yl)-2-butenamine by the procedure of Example 1.

We claim:

1. A method of treating diseases characterized by an imbalance of thromboxane A2 and prostacycline in a mammal which comprises administering internally to said mammal a pharmacologically effective amount of a compound selected from those of the formula:

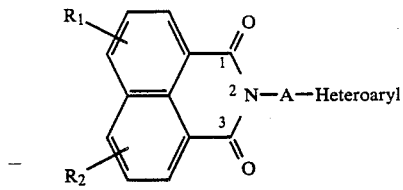

wherein A is a divalent moiety of the formula: —$C_nH_{2n}$— or —$CH_2CH=CHCH_2$— where n is an integer from 3 to 8, inclusive; $R_1$ and $R_2$ may be the same or different and may be selected from the group consisting of hydrogen, halogen, alkoxy having from one to four carbon atoms, alkyl having from one to four carbon atoms, nitro and amino; and where Heteroaryl is

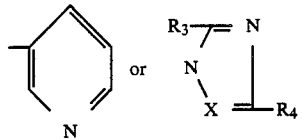

wherein $R_3$ and $R_4$ may be hydrogen, alkyl having from one to four carbon atoms or phenyl; and X is CH or N; together with the pharmaceutically acceptable acid-addition salts thereof.

2. The compound 2-[3-(1H-imidazol-1-yl)propyl]-1H-benz[de]isoquinoline-1,3(2H)-dione.
3. The compound 2-[4-(1H-imidazol-1-yl)butyl]-1H-benz[de]isoquinoline-1,3(2H-dione.
4. The compound 2-[5-(1H-imidazol-1-yl)pentyl]-1H-benz[de]isoquinoline-1,3(2H)-dione.
5. The compound 2-[8-(1H-imidazol-1-yl)octyl]-1H-benz[de]isoquinoline-1,3(2H-dione.
6. The compound 2-[4-(3-pyridinyl)butyl]-1H-benz-[de]isoquinoline-1,3(2H)-dione.
7. The compound 2-[3-(1H-imidazol-1-yl)butyl]-1H-benz[de]isoquinoline-1,3(2H)-dione.
8. The compound 6-amino-2-[4-(1H-imidazol-1-yl)butyl]-1H-benz[de]-isoquinoline-1,3(2H)-dione,dihydrochloride.
9. The compound 2-[3-(1H-imidazol-1-yl)propyl]-5-nitro-1H-benz[de]-isoquinoline-1,3(2H)-dione.
10. The compound -[4-(1H-imidazol-1-yl)butyl]-5-nitro-1H-benz[de]-isoquinoline-1,3(2H)-dione.
11. The compound 5-nitro-2-[3-(1H-1,2,4-triazol-1-yl)propyl]-1H-benzde]isoquinoline-1,3(2H)-dione.
12. The compound 2-[3-(1H-imidazol-1-yl)butyl]-5-nitro-1H-benz[de]-isoquinoline-1,3(2H)-dione.
13. The compound 6-chloro-2-[4-(1H-imida=zol-1-yl)butyl]-1H-benz[de]-isoquinoline-1,3(2H)-dione,-monohydrochloride.
14. A method of inhibiting thromboxane synthetase enzyme in a mammal which comprises administering internally to said mammal a pharmacologically effective amount of a compound selected from those of the formula:

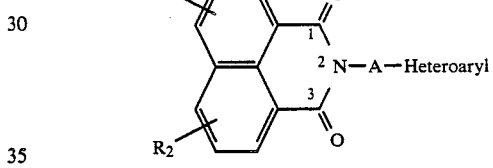

wherein A is a divalent moiety of the formula: —$C_nH_{2n}$— or —$CH_2CH=CHCH_2$— where n is an integer from 3 to 8, inclusive; $R_1$ and $R_2$ may be the same or different and may be selected from the group consisting of hydrogen, halogen, alkoxy having from one to four carbon atoms, alkyl having from one to four carbon atoms, nitro and amino; and where Heteroaryl is

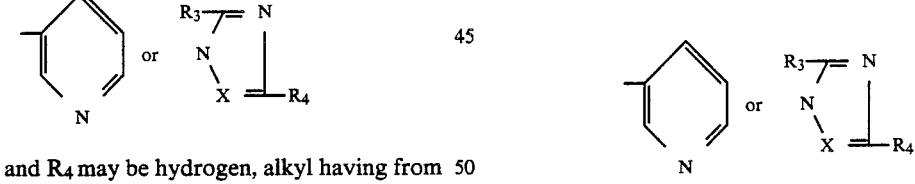

wherein $R_3$ and $R_4$ may be hydrogen, alkyl having from one to four carbon atoms or phenyl; and X is CH or N; together with the pharmaceutically acceptable acid-addition salts thereof.

15. A composition of matter in dosage unit form comprising from about 10 mg to about 700 mg of a compound
2[3-(1H-imidazol-l-yl)propyl]-1H-benz[de]isoquinoline-1,3-4-(1H-imidazol-1-yl)butyl-1H-benz[de]isoquinoline-1,3-(2H-dione;
2[4-(1H-imidazol-1-yl)pentyl-1H-benz -2H)-dione;
2[5-(1H-imidazol-1-yl)octyl-1H-benz isoquinoline-1,3-(2H)-dione;
2-[8-(1H-imidazol-1-yl)octyl]-1-benz[de]isoquinoline-1,3-(2H)-dione;
2[4-(3-pyridinyl)butyl-1H-benz isoquinoline-1,3(2H)-dione;

2[3-(1H-imidazol-1-yl)butyl-1H-benz isoquinoline-1,3-(2H)-dione;

6-amino-2-[4-(1H-imidazol-1-yl)butyl-1H-benz-[de]isoquino-line-1,3(2H)-dione, dihydrochloride;

2-[3-(1H-imidazol-1-yl)propyl-5-nitro-1H-benz isoquino-line-1,3(2H)-dione;

2-[4-(1H-imidazol-1-yl)butyl-5-nitro-1H-benz[de]-isoquino-line-1,3(2H)-dione;

5-nitro-2-[3-(1H-1,2,4-triazol-1-yl)propyl-1H-benz isoquinoline-1, 3(2H)-dione;

2-3-(1H-imidazol-1-yl)butyl-5-nitro-1H-benz-[de]isoquinolineline-1,3(2H)-dione; or 6-chloro-2-[4-(1H-imidazolyl-1-yl)butyl 1H-benze isoquinoline -1,3(2H)-dione, monohydrochloride or the pharmaceutically acceptable acid-addition salts thereof and a pharmaceutically acceptable excipient.

16. A method of lowering elevated blood pressure in a mammal which comprises administering internally to said mammal a pharmacologically effective amount of a compound selected from the group consisting of those of the formula:

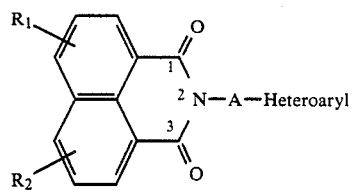

wherein A is a divalent moiety of the formula: $-C_nH_{2n}-$ or $-CH_2CH=CHCH_2-$ where n is an integer from 3 to 8, inclusive; $R_1$ and $R_2$ may be the same or different and may be selected from the group consisting of hydrogen, halogen, alkoxy having from one to four carbon atoms, alkyl having from one to four carbon atoms, nitro and amino; and where Heteroaryl is

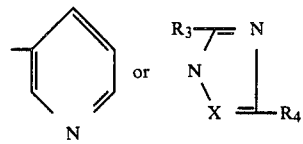

wherein $R_3$ and $R_4$ may be hydrogen, alkyl having from one to four carbon atoms or phenyl; and X is CH or N; together with the pharmaceutically acceptable acid-addition salts thereof.

17. The method according to claim 1 wherein the diease is ischemic heart disease, transient ischemic attack, thrombosis or migrane.

* * * * *